United States Patent

Rose et al.

[11] Patent Number: 6,165,230
[45] Date of Patent: Dec. 26, 2000

[54] 1,4-DIAZACYCLOHEPTANE DERIVATIVES AND THEIR USE IN HAIR OXIDATION DYES

[75] Inventors: David Rose, Hilden; Horst Hoeffkes, Duesseldorf; Bernd Meinigke, Leverkusen, all of Germany

[73] Assignee: Henkel Kommanditgesellschaft auf Aktien, Duesseldorf, Germany

[21] Appl. No.: 09/380,041

[22] PCT Filed: Feb. 20, 1998

[86] PCT No.: PCT/EP98/00986

§ 371 Date: Aug. 25, 1999

§ 102(e) Date: Aug. 25, 1999

[87] PCT Pub. No.: WO98/38175

PCT Pub. Date: Sep. 3, 1998

[30] Foreign Application Priority Data

Feb. 26, 1997 [DE] Germany ............... 197 07 545

[51] Int. Cl.⁷ .................... A61K 7/13; C07D 243/08
[52] U.S. Cl. ............... 8/409; 8/407; 8/416; 8/423; 540/575; 540/609; 540/611; 540/612
[58] Field of Search .................. 8/407, 408, 409, 8/416, 423; 540/557, 575, 609, 611, 612

[56] References Cited

U.S. PATENT DOCUMENTS

| | | | |
|---|---|---|---|
| 4,745,652 | 5/1988 | Rose et al. | 8/409 |
| 4,865,774 | 9/1989 | Fabry et al. | 252/554 |
| 4,931,218 | 6/1990 | Schenker et al. | 252/551 |
| 5,294,726 | 3/1994 | Behler et al. | 554/98 |
| 5,344,464 | 9/1994 | Madrange et al. | 8/410 |
| 5,534,267 | 7/1996 | Neunhoeffer et al. | 424/701 |

FOREIGN PATENT DOCUMENTS

| | | |
|---|---|---|
| 0 008 079 | 2/1980 | European Pat. Off. |
| 0 256 468 | 2/1988 | European Pat. Off. |
| 0 360 644 | 3/1990 | European Pat. Off. |
| 39 26 344 | 2/1991 | European Pat. Off. |
| 0 740 741 | 11/1996 | European Pat. Off. |
| 37 23 354 | 1/1989 | Germany. |
| 37 25 030 | 2/1989 | Germany. |
| 64-61449 | 3/1989 | Japan. |
| WO91/13881 | 9/1991 | WIPO. |
| WO94/08970 | 4/1994 | WIPO. |
| WO98/01434 | 11/1998 | WIPO. |

OTHER PUBLICATIONS

CAPLUS Abstract of JP 1–61449, Terumo Corp., Mar. 1989.
The Science of Hair Care, vol. 7, Chapter 7 pp. 248–250.
Dermatology, 8 pp. 263–287.
Europaeische Inventar der Kosmetic–Rohstoffe, Dittmar et al.

*Primary Examiner*—Caroline D. Liott
*Attorney, Agent, or Firm*—Wayne C. Jaeschke; Glenn E. J. Murphy; Kimberly R. Hild

[57] ABSTRACT

A 1,4-diazacycloheptane derivative and an oxidative hair colorant containing the derivative as a primary intermediate is presented. The 1,4-diazacycloheptane derivative is of the formula:

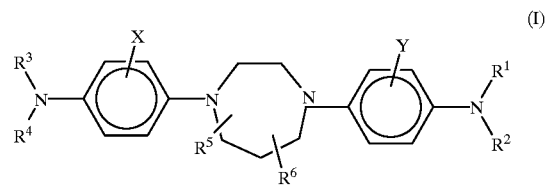

where $R^1$, $R^2$, $R^3$ and $R^4$ independently of one another represent hydrogen, a $C_{1-4}$ alkyl or hydroxyalkyl group or a $C_{2-4}$ dihydroxyalkyl group, X and Y independently of one another represent hydrogen, chlorine, fluorine, a $C_{1-4}$ alkyl, hydroxyalkyl, aminoakyl or alkoxy group, a $C_{2-4}$ dihydroxyalkyl group or an allyl group and $R^5$ and $R^6$ independently of one another represent hydrogen or a $C_{1-4}$ alkyl group. Natural color tones can be obtained in keratin fibers with oxidative hair colorants containing the 1,4-diazacycloheptane derivative, without the use of additional primary intermediates.

17 Claims, No Drawings

1,4-DIAZACYCLOHEPTANE DERIVATIVES AND THEIR USE IN HAIR OXIDATION DYES

This application is filed under 35 U.S.C. 371 and based on PCT/EP98/00986, filed Feb. 20, 1998.

BACKGROUND OF THE INVENTION

1. Field of the Invention

This invention relates to new diazacycloheptane derivatives, to their use for coloring keratin fibers and to colorants containing these compounds.

2. Discussion of Related Art

By virtue of their intensive colors and good fastness properties, so-called oxidation colorants play a prominent role in the coloring of keratin fibers, particularly human hair. Oxidation colorants contain oxidation dye precursors, so-called primary intermediates and secondary intermediates. The primary intermediates form the actual dyes with one another or by coupling with one or more secondary intermediates in the presence of oxidizing agents or atmospheric oxygen.

Good oxidation dye precursors are expected to satisfy above all the following requirements: they must form the required color tones with sufficient intensity and fastness during the oxidative coupling reaction. In addition, they must be readily absorbed onto the fibers with no significant differences—particularly in the case of human hair—between damaged and freshly regrown hair (levelling behavior). They must be resistant to light, heat and the effect of chemical reducing agents, for example permanent wave lotions. Finally, if they are used to color hair, they should not overly stain the scalp and, above all, should be toxicologically and dermatologically safe.

The primary intermediates normally used are primary aromatic amines containing another free or substituted hydroxy or amino group in the para position or the ortho position, diaminopyridine derivatives, heterocyclic hydrazones, 4-aminopyrazolone derivatives and 2,4,5,6-tetraaminopyrimidine and derivatives thereof.

Special representatives are, for example, p-phenylenediamine, p-toluylenediamine, 2,4,5,6-tetraaminopyrimidine, p-aminophenol, N,N-bis-(2-hydroxyethyl)-p-phenylenediamine, 2-(2,5-diaminophenyl)-ethanol, (2-(2,5-diaminophenoxy)-ethanol, 1-phenyl-3-carboxyamido-4-amino-5-pyrazolone, 4-amino-3-methylphenol, 2-aminomethyl-4-aminophenol, 2-hydroxy-4,5,6-triaminopyrimidine, 2,4-dihydroxy-5,6-diaminopyrimidine, 2,5,6-triaminohydroxy pyrimidine and 1,3-N,N'-bis-(2'-hydroxyethyl)-N,N'-bis-(4'-aminophenyl)-diamino-2-propanol.

The secondary intermediates are generally m-phenylenediamine derivatives, naphthols, resorcinol and resorcinol derivatives, pyrazolones and m-aminophenols. Particularly suitable secondary intermediates are 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 2-chlororesorcinol, 4-chlororesorcinol, 2-chloro-6-methyl-3-aminophenol, 2-amino-4-hydroxypyridine, 2-methyl resorcinol and 5-methyl resorcinol.

In general, natural color tones cannot be obtained with a primary intermediate alone or with a special secondary intermediate/primary intermediate combination. In practice, therefore, combinations of various primary intermediates and secondary intermediates are used so that there is a constant need for new improved dye components.

Accordingly, the problem addressed by the present invention was to provide new primary intermediates which would satisfy the requirements oxidation dye precursors are expected to meet to a particular degree.

DESCRIPTION OF THE INVENTION

It has now been found that certain, hitherto unknown 1,4-diazacycloheptane derivatives satisfy the requirements primary intermediates are expected to meet to a particularly high degree. Thus, brilliant color tones, more especially in the brown and blue range, which are extremely fast to light and washing are obtained using these primary intermediates with most of the known secondary intermediates. In addition, the colors obtained are distinguished by extremely high fastness to cold waving and thermal stability and by excellent level dyeing behavior.

In a first embodiment, therefore, the present invention relates to 1,4-diazacycloheptane derivatives corresponding to general formula (I):

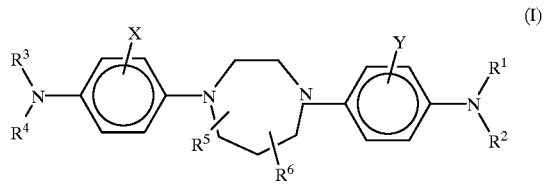

$R^1$, $R^2$, $R^3$ and $R^4$ independently of one another represent hydrogen, a $C_{1-4}$ alkyl or hydroxyalkyl group or a $C_{2-4}$ dihydroxyalkyl group, X and Y independently of one another represent hydrogen, chlorine, fluorine, a $C_{1-4}$ alkyl, hydroxyalkyl, aminoalkyl or alkoxy group, a $C_{2-4}$ dihydroxyalkyl group or an allyl group and $R^5$ and $R^6$ independently of one another represent hydrogen or a $C_{2-4}$ alkyl group.

These compounds can be produced by known organic synthesis methods. Particulars can be found in the following Synthesis Examples.

The outstanding suitability of these compounds as primary intermediates for oxidation colorants is also particularly surprising because the analogous piperidino compounds do not have any significant primary intermediate properties.

Since all the compounds according to the invention are amino compounds, the known acid addition salts can be prepared from them by the usual methods. Accordingly, all the disclosures of the present specification and, hence, the claimed scope of protection apply both to the 1,4-diazacycloheptane derivatives of formula (I) present in free form and to their water-soluble, physiologically compatible salts. Examples of such salts are the hydrochlorides, the hydrobromides, the sulfates, the phosphates, the acetates, the propionates, the citrates and the lactates.

The 1,4-diazacycloheptane derivatives corresponding to formula (I), in which the two substituents $R^5$ and $R^6$ at the 1,4-diazacycloheptane ring are hydrogens, have proved to be particularly suitable for the purposes of the invention.

Compounds corresponding to formula (I), in which at least three and, more particularly, all four of the groups $R^1, R^2, R^3$ and $R^4$ are hydrogens, are also preferred for the purposes of the invention.

Finally, those 1,4-diazacycloheptane derivatives of formula (I) in which the two substituents X and Y at the two aromatic rings independently of one another represent hydrogen, fluorine, chlorine or a $C_{1-4}$ alkyl group, have also proved to be particularly suitable for the purposes of the invention. Hydrogen and methyl groups have proved to be most particularly advantageous groups X and Y.

Compounds with particularly outstanding suitability for the purposes of the invention are N,N'-bis-(4-aminophenyl)-1,4-diazacycloheptane,
N,N'-bis-(4-amino-2-methylphenyl)-1,4-diazacycloheptane and
N,N'-bis-(4-amino-3-methylphenyl)-1,4-diazacycloheptane.

Of these compounds, N,N'-bis-(4-aminophenyl)-1,4-diazacycloheptane and N,N'-bis-(4-amino-3-methylphenyl)-1,4-diazacycloheptane are preferred.

In a second embodiment, the present invention relates to the use of the above-mentioned 1,4-diazacycloheptane derivatives as primary intermediates in oxidation hair colorants.

Finally, in a third embodiment, the present invention relates to oxidation colorants for coloring keratin fibers containing secondary intermediates and primary intermediates in a water-containing carrier, characterized in that one of the above-mentioned 1,4-diazacycloheptane derivatives is present as the primary intermediate.

Keratin fibers in the context of the present invention include pelts, wool, feathers and, more particularly, human hair. Although the oxidation colorants according to the invention are particularly suitable for coloring keratin fibers, there is basically nothing to prevent them from being used in other fields, particularly in color photography.

The oxidation colorants according to the invention contain the primary intermediates according to the invention and, if desired, may contain other primary intermediates and secondary intermediates. So far as the other primary and secondary intermediates are concerned, reference is made to the compounds mentioned at the beginning of the present specification which represent preferred other dye components.

According to the invention, preferred primary intermediates are p-phenylenediamine, p-toluylenediamine, p-aminophenol, o-aminophenol, 1-(2'-hydroxyethyl)-2,5-diaminobenzene, N,N-bis-(2-hydroxyethyl) p-phenylenediamine, 2-(2,5-diaminophenoxy)-ethanol, 1-phenyl-3-carboxyamido-4-amino-5-pyrazolone, 4-amino-3-methylphenol, 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxyethylaminomethyl-4-aminophenol, 4,4'-diaminodiphenylamine, 4-amino-3-fluorophenol, 2-aminomethyl-4-aminophenol, 2-hydroxymethyl-4-aminophenol, bis-(2-hydroxy-5-aminophenyl)-methane, 1,4-bis-(4-aminophenyl)-diazacycloheptane, 1,3-bis-(N-(2-hydroxyethyl)-N-(4-aminophenylamino))-2-propanol, 4-amino-2-(2-hydroxyethoxy)-phenol and 4,5-diaminopyrazole derivatives according to EP 0 740 741 or WO 94/08970 such as, for example, 4,5-diamino-1-(2'-hydroxyethyl)-pyrazole.

Most particularly preferred other primary intermediates are 2,4,5,6-tetraminopyrimidine, 1-(2'40-hydroxyethyl)-2,5-diaminobenzene, 3-methyl-4-aminophenol, o-aminophenol, 2-aminomethyl- and 2-hydroxymethyl-4-aminophenol.

According to the invention, preferred secondary intermediates are 1-naphthol, pyrogallol, 1,5-, 2,7- and 1,7-dihydroxynaphthalene, o-aminophenol, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 4-chlororesorcinol, 2-chloro-6-methyl-3-aminophenol, 2-methyl resorcinol, 5-methyl resorcinol, 2,5-dimethyl resorcinol, 2,6-dihydroxypyridine, 2,6-diaminopyridine, 2-amino-3-hydroxypyridine, 2,6-dihydroxy3,4-diaminopyridine, 3-amino-2-methylamino-6-methoxypyridine, 4-amino-2-hydroxytoluene, 2,6-bis-(2-hydroxyethylamino)-toluene, 2,4-diaminophenoxyethanol, 1-methoxy-2-amino-4-(2-hydroxyethylamino)-benzene, 2-methyl-4-chloro-5-aminophenol, 6-methyl-1,2,3,4-tetrahydroquinoxaline, 3,4-methylenedioxyphenol, 3,4-methylenedioxyaniline, 2,6-dimethyl-3-aminophenol, 3-amino-6-methoxy-2-methylaminophenol, 2-hydroxy-4-aminophenoxyethanol, 2-methyl-5-(2-hydroxyethylamino)-phenol and 2,6-dihydroxy-3,4-dimethyl pyridine.

Particularly preferred secondary intermediates are 1-naphthol, resorcinol, 1,3-bis-(2,4-diaminophenoxy)-propane, 2-hydroxy-4-aminophenoxyethanol, 4-chlororesorcinol, 2,4-diaminophenoxyethanol, 2-methyl resorcinol, 2-methyl-5-(2-hydroxyethylamino)-phenol, 3-amino-2-methylamino-6-methoxypyridine.

These other primary and secondary intermediates are normally used in free form. Where they contain amino groups, however, it may be preferable to use them in salt form, particularly in the form of the hydrochlorides and sulfates.

The hair colorants according to the invention contain both the primary intermediates and the secondary intermediates in a quantity of preferably 0.005 to 20% by weight and more preferably 0.1 to 5% by weight, based on the oxidation colorant as a whole. The primary intermediates and secondary intermediates are generally used in a substantially equimolar ratio to one another. Although it has proved to be of advantage to use the primary and secondary intermediates in an equimolar ratio, there is no disadvantage in using individual oxidation dye precursors in a certain excess so that primary intermediates and secondary intermediates may be present in a molar ratio of 1:0.5 to 1:3 and, more particularly, 1:1 to 1:2.

Substantive dyes are normally nitrophenylendiamines, nitroaminophenols, aza dyes, anthraquinones or indophenols. Preferred substantive dyes are the compounds known under the International names or trade names of HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene. The colorants according to the invention of this embodiment preferably contain the substantive dyes in a quantity of 0.01 to 20% by weight, based on the colorant as a whole.

The colorants according to the invention may also contain naturally occurring dyes such as, for example, henna red, henna neutral, henna black, camomile blossom, sandalwood, black tea, black alder bark, sage, logwood, madder root, catechu, sedre and alkanet.

Other dye components which may be present in the colorants according to the invention are indols and indolines and physiologically compatible salts thereof. Preferred examples are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 6-hydroxyindole, 6-aminoindole and 4-aminoindole. Also preferred are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 6-hydroxyindoline, 6-aminoindoline and 4-aminoindoline.

The oxidation dye precursors or the substantive dyes optionally present do not have to be single compounds. On the contrary, other components may be present in small quantities in the hair colorants according to the invention due to the processes used to produce the individual dyes providing these other components do not adversely affect the coloring result or have to be ruled out for other reasons, for example toxicological reasons.

So far as the dyes suitable for use in the hair colorants and tinting formulations according to the invention are concerned, reference is also expressly made to the work by Ch. Zviak, The Science of Hair Care, Chapter 7 (pages 248–250; substantive dyes) and Chapter 8, pages 264–267; oxidation dye precursors), published as Volume 7 of the Series "Dermatology" (Ed.: Ch. Culnan and H. Maibach), Marcel Dekker Inc., New York/Basle, 1986, and to the "Europäische Inventar der Kosmetik-Rohstoffe" published by the Europäische Gemeinschaft and available in disk form from the Bundesverband Deutscher Industrie- und Handelsunternehmen für Arzneimittel, Reformwaren und Körperpflegemittel d.V., Mannheim.

To produce the colorants according to the invention, the oxidation dye precursors are incorporated in a suitable water-containing carrier. For coloring hair, such carriers are, for example, creams, emulsions, gels or even surfactant-containing foaming solutions, for example shampoos, foam aerosols or other formulations suitable for application to the hair.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the hair colorants according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide and hydroxyl groups may also be present in the molecule. The following are examples of suitable anionic surfactants—in the form of the sodium, potassium and ammonium salts and the mono-, di- and trialkanol-ammonium salts containing 2 or 3 carbon atoms in the alkanol group:

linear fatty acids containing 10 to 22 carbon atoms (soaps),
ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16,
acyl sarcosides containing 10 to 18 carbon atoms in the acyl group,
acyl taurides containing 10 to 18 carbon atoms in the acyl group,
acyl isethionates containing 10 to 18 carbon atoms in the acyl group,
sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups,
linear alkane sulfonates containing 12 to 18 carbon atoms,
linear α-olefin sulfonates containing 12 to 18 carbon atoms,
α-sulfofatty acid methyl esters of fatty acids containing 12 to 18 carbon atoms,
alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids containing 12 to 24 carbon atoms and 1 to 6 double bonds according to DE-A-39 26 344,
esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated C$_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a C$_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and C$_{12-18}$ acyl sarcosine.

Nonionic surfactants contain, for example, a polyol group, a polyalkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 moles of ethylene oxide onto glycerol, $C_{8-22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone/ vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/ dimethyl diallyl ammonium chloride copolymers, dimethyl aminoethyl methacrylate/vinyl pyrrolidone copolymers quaternized with diethyl sulfate, vinyl pyrrolidone/ imidazolinium methochloride copolymers and quaternized polyvinyl alcohol, zwitterionic and amphoteric polymers such as, for example, acrylamidopropyl/trimethyl ammonium chloride/acrylate copolymers and octyl acrylamide/methyl methacrylate/ tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/ vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, carob bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, antidandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, UV absorbers, consistency providers, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, pearlescers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

In principle, the color can be oxidatively developed with atmospheric oxygen. However, a chemical oxidizing agent is preferably used, particularly when human hair is to be not only colored, but also lightened. Particularly suitable oxidizing agents are persulfates, chlorites and, in particular, hydrogen peroxide or addition products thereof with urea, melamine or sodium borate. Oxidation may also be carried out with enzymes. In this case, the enzymes may be used to transfer atmospheric oxygen to the primary intermediate or to enhance the effect of an oxidizing agent present in small quantities. One example of an enzymatic process is the procedure whereby the effect of small quantities (for example 1% and less, based on the formulation as a whole) of hydrogen peroxide is enhanced by peroxidases.

The preparation of the oxidizing agent is preferably mixed with the preparation of the oxidation dye precursors immediately before coloring of the hair. The ready-to-use hair coloring preparation formed should preferably have a pH value in the range from 6 to 10. In a particularly preferred embodiment, the hair colorant is used in a mildly alkaline medium. The application temperatures may be in the range from 15 to 40° C. After a contact time of about 5 to 30 minutes, the hair colorant is removed from the hair to be colored by rinsing. There is no need for the hair to be washed with a shampoo where a carrier of high surfactant content, for example a coloring shampoo, has been used.

The following Examples are intended to illustrate the invention.

EXAMPLES

1. Synthesis Examples 1.1. Synthesis of N,N'-bis-(4-aminophenyl)-1,4-diazacycloheptane-4 HCI 1st Stage: N,N'-bis-(4-nitrophenyl)-1,4-diazacycloheptane A mixture of 22 g of 1,4-diazacycloheptane, 28.2 g of p-fluoronitrobenzene and 300 ml of ethanol was heated for 6 hours to 150° C. in an autoclave. After cooling, the solid precipitated was filtered off under suction. The product accumulated in the form of yellow crystals with a melting point of >310° C.

2nd Stage: N,N'-bis-(4-aminophenyl)-1,4-diazacycloheptane-4 HCI 14.8 g of the product from stage 1 were suspended in 300 ml of a 1:1 mixture of ethanol and water. The resulting suspension was then hydrogenated under a hydrogen pressure of 20 atm and at a temperature of 50° C. using a conventional catalyst (palladium on carbon) until no more hydrogen was taken up. After cooling, the catalyst was filtered off and the solution was acidified with dilute hydrochloric acid and concentrated by evaporation to dryness. The product accumulated in the form of light violet crystals with a melting point of 196° C. (decomp.).

2.1. Synthesis of N,N'-bis-(4-amino-2-methylphenyl)-1,4-diazacycloheptane-4 HCI

1st Stage: N,N'-bis-(4-nitro-2-methylphenyl)-1,4-diazacycloheptane

A mixture of 7.9 g of 1,4-diazacycloheptane, 24.1 g of 2-fluoro-5-nitrotoluene and 300 ml of ethanol was heated for 6 hours to 150° C. in an autoclave. After cooling, the solid precipitated was filtered off under suction. The product accumulated in the form of yellow crystals with a melting point of 154° C.

2nd Stage: N,N'-bis-(4-amino-2-methylphenyl)-1,4-diazacycloheptane-4 HCI 3.5 g of the product from stage 1 was suspended in 400 ml of ethanol. The resulting suspension was then hydrogenated under a hydrogen pressure of 5 atm and at a temperature of 50° C. using a conventional catalyst (palladium on carbon) until no more hydrogen was taken up. After cooling, the catalyst was filtered off, the solution was acidified with dilute hydrochloric acid and concentrated by evaporation to dryness. The product accumulated in the form of colorless crystals melting at around 220° C. (decomp.).

3.1. Synthesis of N,N'-bis-(4-amino-3-methylphenyl)-1,4-diazacycloheptane-4 HCI

1st Stage: N,N'-bis-(4-nitro-3-methylphenyl)-1,4-diazacycloheptane

A mixture of 16.6 g of 1,4-diazacycloheptane, 52 g of 5-fluoro-2-nitrotoluene and 300 ml of ethanol was heated for 6 hours to 150° C. in an autoclave. After cooling, the solid precipitated was filtered off under suction. The product accumulated in the form of yellow crystals with a melting point of 214° C.

2nd Stage: N,N'-bis-(4-amino-3-methylphenyl)-1,4-diazacycloheptane-4 HCI 3.5 g of the product from stage 1 were suspended in 400 ml of ethanol. The resulting suspension was then hydrogenated under a hydrogen pressure of 5 atm and at a temperature of 50° C. using a conventional catalyst (palladium on carbon) until no more hydrogen was taken up. After cooling, the catalyst was filtered off and the solution was acidified with dilute hydrochloric acid and concentrated by evaporation to dryness. The product accumulated in the form of beige-colored crystals with a melting point of 182° C. (decomp.).

2. Coloring

A cream base with the following composition was first prepared [all quantities are in g, unless otherwise indicated]:

| | |
|---|---|
| tallow fatty alcohol | 17.0 |
| Lorol ® techn.[1] | 4.0 |
| Texapon ® N 28[2] | 40.0 |
| Dehyton ® K[3] | 25.0 |
| Eumulgin ® B 2[4] | 1.5 |
| distilled water | 12.5 |

[1]$C_{12-18}$ fatty alcohol (HENKEL)
[2]Sodium lauryl ether sulfate (ca. 28% active substance; CTFA name: Sodium Laureth Sulfate) (HENKEL)
[3]Fatty acid amide derivative with a betaine structure corresponding to the following formula: R—$CONH(CH_2)_3N^+(CH_3)_2CH_2COO^-$ (ca. 30% active substance; CTFA name Cocoamidopropyl Betaine) (HENKEL)
[4]Cetyl stearyl alcohol containing ca. 20 moles EO (CTFA name: Ceteareth-20) (HENKEL)

The following hair coloring cream emulsion was then prepared on the basis of this cream:

| | |
|---|---|
| cream base | 50.0 |
| primary intermediate | 7.5mmoles* |
| secondary intermediate | 7.5mmoles* |
| Na₂SO₃ (inhibitor) | 1.0 |
| (NH₄)₂SO₄ | 1.0 |
| conc. ammonia solution to | pH 10 |
| water to | 100 |

*unless otherwise indicated

The ingredients were mixed in the order listed. After addition of the oxidation dye precursors and the inhibitor, the emulsion was first adjusted to pH 10 with concentrated ammonia solution and was then made up with water to 100 g.

The color was oxidatively developed with 3% hydrogen peroxide solution as the oxidizing solution. To this end, 50 g of hydrogen peroxide solution (3%) were added to and mixed with 100 g of the emulsion.

The coloring cream was applied to approximately 5 cm long tresses of standardized, 90% grey but not specially pretreated human hair and left thereon for 30 minutes at 32° C. On completion of the coloring process, the hair was rinsed, washed with a normal shampoo and dried. The following primary and secondary intermediates were used for coloring:

Primary intermediates
N,N'-bis-(4-aminophenyl)-1,4-diazacycloheptane (P1)
N,N'-bis-(4-aminophenyl)-piperidine (P2)—Comparison Example—
N,N'-bis-(4-amino-2-methylphenyl)-1,4-diazacycloheptane (P3)
N,N'-bis-(4-amino-3-methylphenyl)-1,4-diazacycloheptane (P4)
2,4,5,6-tetraaminopyrimidine (P5)
4-amino-3-methylphenol (P6)
2-aminomethyl-4-aminophenol (P7)
p-aminophenol (P8)
1-(2-hydroxyethyl)-2,5-diaminobenzene (P9)
4-hydroxy-2,5,6-triaminopyrimidine (P10)
N,N-bis-(2-hydroxyethyl)-p-phenylenediamine (P11)
p-toluylenediamine (P12)
2-(2,5-diaminophenoxy)-ethanol (P13).
Secondary intermediates
1-naphthol (S1)
rescorcinol (S2)
2-methyl-5-aminophenol (S3)
1,3-bis-(2,4-diaminophenoxy)-propane (S4)
2-chloro-6-methyl-3-aminophenol (S5)
3-amino-6-methoxy-2-methylaminophenol (S6)
2-hydroxy-4-aminophenoxyethanol (S7)
2-amino-3-hydroxypyridine (S8)
4-chlororesorcinol (S9)
2,4-diaminophenoxyethanol (S10)
2,6-dimethyl-3-aminophenol (S11)
2,4-dichloro-3-aminophenol (S12)
3,4-methylenedioxyphenol (S13)
2-methyl resorcinol (S14)
m-aminophenol (S15)
2-methyl-5-(2-hydroxyethylamino)-phenol (S16)
2,6-dihydroxy-3,4-dimethyl pyridine (S17)
3-amino-2-methylamino-6-methoxypyridine (S18)
1-methoxy-2-amino-4-(2-hydroxyethylamino)-benzene (S19)
2,6-bis-(2-hydroxyethylamino)-toluene (S20)
1,7-dihydroxynaphthalene (S21)
2,7-dihydroxynaphthalene (S22)

The following colors were obtained:

| Primary intermediate | Secondary intermediate | Hair color | Intensity |
|---|---|---|---|
| P1 | S1 | Azure blue | Very intensive |
| P2 | S1 | Grey-magenta | Very weak |
| P1 | S2 | Dark brown | Intensive |
| P2 | S2 | Dark blond | Weak |
| P1 | S3 | Dark violet | Intensive |
| P2 | S3 | Red-brown | Very weak |
| P1 | S4 | Black-blue | Very intensive |
| P2 | S4 | Dark violet | Very weak |
| P1 | S5 | Dark violet | Very intensive |
| P2 | S5 | Violet | Very weak |
| P1 | S7 | Dark violet | Intensive |
| P1 | S8 | Dark violet | Intensive |
| P1 | S9 | Grey-brown | Intensive |
| P1 | S10 | Black-blue | Intensive |
| P1 | S11 | Deep violet | Intensive |
| P1 | S12 | Black-blue | Intensive |
| P1 | S13 | Grey-brown | Intensive |
| P1 | S14 | Dark brown | Intensive |
| P1 | S15 | Black-blue | Intensive |
| P1 | S16 | Dark violet | Intensive |
| P1 | S17 | Grey-blue | Intensive |
| P1 | S18 | Dark green | Intensive |
| P1 | S19 | Black-blue | Intensive |
| P3 | S1 | Flat red | Intensive |
| P3 | S5 | Grey-red | Intensive |
| P4 | S4 | Dark blue | Intensive |
| P4 | S5 | Black-blue | Intensive |
| P4 | S6 | Dark turquoise | Intensive |
| P1 + P5ᵃ | S4 + S14ᵃ | Dark blue | Intensive |
| P1 + P6ᵃ | S8 | Red-brown | Intensive |
| P1 + P7ᵃ | S3 | Photobrown | Intensive |
| P1 + P8ᵃ | S3 | Photobrown | Intensive |
| P1 + P9ᵃ | S3 | Dark violet | Intensive |
| P1 + P10ᵃ | S20 | Black-blue | Intensive |
| P1 + P11ᵃ | S2 + S15ᵃ | Blue-grey | Intensive |
| P1 + P8ᵃ | S4 + S9ᵃ | Navy blue | Intensive |
| P1 + P10ᵃ | S11 + S21ᵃ | Dark violet | Intensive |
| P1 + P12ᵃ | S18 + S22ᵃ | Nordic blue | Intensive |
| P1 + P6ᵃ + P13ᵃ | S3ᵇ | Dark ruby | Intensive |

ᵃ0.375 mmole
ᵇ0.113 mmole

What is claimed is:

1. A 1,4-diazacycloheptane derivative comprising compounds of the formula (I):

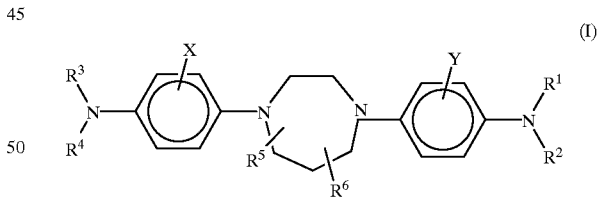

or a physiologically compatible salt thereof, wherein $R^1$, $R^2$, $R^3$ and $R^4$ independently of one another represent hydrogen, a $C_{1-4}$ alkyl or hydroxyalkyl group or a $C_{2-4}$ dihydroxyalkyl group, X and Y independently of one another represent hydrogen, chlorine, fluorine, a $C_{1-4}$ alkyl, hydroxyalkyl, aminoalkyl or alkoxy group, a $C_{2-4}$ dihydroxyalkyl group or an allyl group, and $R^5$ and $R^6$ independently of one another represent hydrogen or a $C_{1-4}$ alkyl group.

2. The 1,4-diazacycloheptane derivative of claim 1 wherein both $R^5$ and $R^6$ are hydrogen atoms.

3. The 1,4-diazacycloheptane derivative of claim 1 wherein at least three of the substituents $R^1$, $R^2$, $R^3$ and $R^4$ are hydrogen atoms.

4. The 1,4-diazacycloheptane derivative of claim 1 wherein X and Y independently of one another represent hydrogen, or a methyl group.

5. The 1,4-diazacycloheptane derivative of claim 1 comprising N,N'-bis-(4-aminophenyl)-1,4-diazacycloheptane or N,N'-bis-(4-amino-3-methylphenyl)-1,4-diazacycloheptane.

6. The 1,4-diazacycloheptane derivative of claim 1 wherein said derivative is in the form of a water-soluble salt.

7. The 1,4-diazacycloheptane derivative of claim 6 comprising a hydrochloride, hydrobromide, sulfate, phosphate, acetate, propionate, citrate or lactate salt.

8. An oxidative hair colorant composition comprising a 1,4-diazacycloheptane derivative of the formula (I):

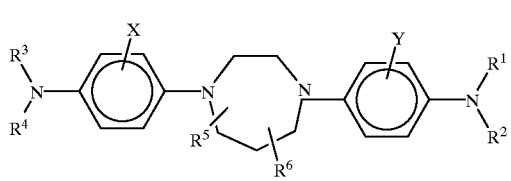

wherein $R^1$, $R^2$, $R^5$ and $R^4$ independently of one another represent hydrogen, a $C_{1-4}$ alkyl or hydroxyalkyl group or a $C_{2-4}$ dihydroxyalkyl group, X and Y independently of one another represent hydrogen, chlorine, fluorine, a $C_{1-4}$ alkyl, hydroxyalkyl, aminoalkyl or alkoxy group, a $C_{2-4}$ dihydroxyalkyl group or an allyl group, and $R^5$ and $R^6$ independently of one another represent hydrogen or a $C_{1-4}$ alkyl group as a primary intermediate.

9. The hair colorant composition of claim 8 wherein the 1,4-diazacycloheptane derivative comprises N,N'-bis-(4-aminophenyl)-1,4-diazacycloheptane, N,N'-bis-(4-amino-2-methylphenyl)-1,4-diazacycloheptane, or N,N'-bis-(4-amino-3-methylphenyl)-1,4-diazacycloheptane.

10. The hair colorant composition of claim 8 further comprising a secondary intermediate and a water-containing carrier.

11. The hair colorant composition of claim 10 wherein the secondary intermediate is selected from the group consisting of 1-naphthol, resorcinol, 1,3-bis-(2,4-diaminophenoxy)-propane, 2-hydroxy-4-aminophenoxyethanol, 4-chlororesorcinol, 2,4-diaminophenoxyethanol, 2-methyl resorcinol, 2-methyl-5-(2-hydroxyethylamino)-phenol, and 3-amino-2-methylamino-6-methoxypyridine.

12. The hair colorant composition of claim 8 further comprising at least one primary intermediate in addition to said 1,4-diazacycloheptane derivative.

13. The hair colorant composition of claim 12 wherein the additional primary intermediate is selected from the group consisting of 2,4,5,6-tetraaminopyrimidine, 4-hydroxy-2,5,6-triaminopyrimidine, 1-(2-hydroxyethyl)-2,5-diaminobenzene, p-phenylenediamine, p-toluylenediamine, p-aminophenol, 3-methyl-p-aminophenol, 2-aminomethyl-p-aminophenol and 1,3-N,N'-bis-(2'-hydroxyethyl)-N,N'-bis-(4'-aminophenyl)-diamino-1,3-propan-2-ol.

14. The hair colorant composition of claim 8 comprising 0.005 to 20 percent by weight of primary intermediates and 0.005 to 20 percent by weight of secondary intermediates.

15. The hair colorant composition of claim 14 comprising 0.1 to 5 percent by weight of primary intermediates and 0.1 to 5 percent by weight of secondary intermediates.

16. The hair colorant composition of claim 8 further comprising at least one substantive dye.

17. A process for coloring a keratin fiber comprising contacting a keratin fiber with an oxidative colorant composition comprising a 1,4-diazacycloheptane derivative of the formula (I):

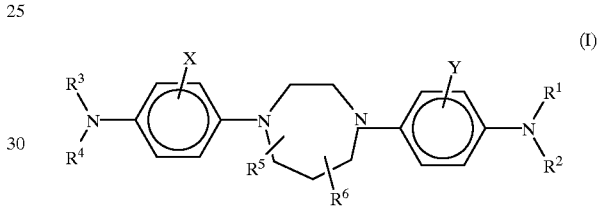

wherein $R^1$, $R^2$, $R^3$ and $R^4$ independently of one another represent hydrogen, a $C_{1-4}$ alkyl or hydroxyalkyl group or a $C_{2-4}$ dihydroxyalkyl group, X and Y independently of one another represent hydrogen, chlorine, fluorine, a $C_{1-4}$ alkyl, hydroxyalkyl, aminoalkyl or alkoxy group, a $C_{2-4}$ dihydroxyalkyl group or an allyl group, and $R^5$ and $R^6$ independently of one another represent hydrogen or a $C_{1-4}$ alkyl group.

* * * * *